US010092003B2

(12) United States Patent
Widder et al.

(10) Patent No.: US 10,092,003 B2
(45) Date of Patent: Oct. 9, 2018

(54) INSECT CONTROL DEVICE AND ASSOCIATED METHODS

(71) Applicant: Novel Textiles & Treatments LLC, New York, NY (US)

(72) Inventors: Laurie Widder, New York, NY (US); Gary Innocenti, Sr., Mahwah, NJ (US)

(73) Assignee: Novel Textiles & Treatments LLC, New York, NY (US)

( * ) Notice: Subject to any disclaimer, the term of this patent is extended or adjusted under 35 U.S.C. 154(b) by 0 days.

(21) Appl. No.: 14/716,723

(22) Filed: May 19, 2015

(65) Prior Publication Data

US 2015/0359227 A1  Dec. 17, 2015

Related U.S. Application Data

(60) Provisional application No. 62/000,979, filed on May 20, 2014.

(51) Int. Cl.
*A01N 53/00* (2006.01)

(52) U.S. Cl.
CPC .................................. *A01N 53/00* (2013.01)

(58) Field of Classification Search
CPC ..... A61N 53/00; A01N 25/18; A01N 2300/00
See application file for complete search history.

(56) References Cited

U.S. PATENT DOCUMENTS

| | | | |
|---|---|---|---|
| 3,295,246 A | 1/1967 | Landsman et al. | |
| 4,767,812 A | 8/1988 | Chapin et al. | |
| 6,015,570 A * | 1/2000 | Tucci ..................... | A01N 25/18 424/403 |
| 6,162,454 A * | 12/2000 | Ahr ........................ | A01N 25/18 424/403 |
| 6,534,079 B1 * | 3/2003 | Munagavalasa ....... | A01N 53/00 424/409 |
| 6,551,560 B1 * | 4/2003 | Flashinski ............ | A01M 1/2077 219/392 |
| 6,582,714 B1 * | 6/2003 | Emmrich ............... | A01N 53/00 424/405 |
| 6,803,051 B1 * | 10/2004 | Voris ...................... | A01N 53/00 424/403 |
| 2005/0132500 A1 * | 6/2005 | Karl ....................... | A01N 25/10 8/115.51 |
| 2009/0010977 A1 | 1/2009 | Xin et al. | |
| 2012/0064323 A1 * | 3/2012 | Shoemake ............... | C08J 5/043 428/220 |
| 2013/0251773 A1 * | 9/2013 | Galiatsatos ............ | A01N 25/18 424/403 |
| 2013/0280314 A1 * | 10/2013 | Ansley ..................... | E04B 1/72 424/412 |
| 2014/0048617 A1 * | 2/2014 | Furner ................. | A01M 7/0003 239/55 |

FOREIGN PATENT DOCUMENTS

| | | |
|---|---|---|
| WO | WO 97/29638 A1 | 8/1997 |
| WO | WO 01/58261 A2 | 8/2001 |
| WO | WO 2013/180984 A1 | 12/2013 |
| WO | WO 2015/179440 A1 | 11/2015 |

OTHER PUBLICATIONS

International Search Report and Written Opinion for PCT/US2015/031630, dated Jul. 31, 2015.
International Preliminary Report on Patentability for PCT/US2015/031630 dated Dec. 1, 2016.
Argueta et al., Spatial repellency of metofluthrin-impregnated multilayer paper strip against Aedes albopictus under outdoor conditions, Nagasaki, Japan. Med. Entomol. Zool. 2004;55(3):211-6.

* cited by examiner

*Primary Examiner* — Doan T Phan
(74) *Attorney, Agent, or Firm* — Wolf, Greenfield & Sacks, P.C.

(57) ABSTRACT

Insect control devices and associated methods are generally described. In some embodiments, the insect control device includes one or more substrate materials impregnated or otherwise loaded with an active species (e.g., a pyrethroid). In some cases, the device may provide protection against insects over prolonged periods of time.

23 Claims, 12 Drawing Sheets

ICT CONTROL DEVICE AND
ASSOCIATED METHODS

RELATED APPLICATIONS

This application claims priority under 35 U.S.C. § 119(e) to U.S. Provisional Patent Application Ser. No. 62/000,979, filed May 20, 2014, and entitled "Insect Control Device and Associated Methods," which is incorporated herein by reference in its entirety for all purposes.

GOVERNMENT LICENSE RIGHTS

This invention was made with government support under Contract Number W81XXXWH-14-C-0005 awarded by the Department of Defense—OSD Defense Health Program SBIR Program. The government has certain rights in the invention.

FIELD

Insect control devices and associated methods are generally described.

BACKGROUND

Insecticidal agents are generally effective in repelling, knocking down, and/or killing many disease-carrying insects such as arthropods. For example, Transfluthrin is a vapor-active pyrethroid compound that delivers efficacy against flying arthropods. Solutions of transfluthrin are often used in household products for controlling flying insects, many of which rely on temporary spraying or heat-diffused systems for pyrethroid release or distribution. However, these solutions can produce an unpleasant odor and/or cause respiratory irritation. Currently available devices for delivery of pyrethroid compounds can also be bulky, heavy, and difficult to pack and carry, and often require electricity to heat and/or activate pyrethroid release (e.g., a Liquid Emanatory Device (LED)) or burned (e.g. mosquito coil). Additionally, these solutions and devices often provide an undesirably limited length of time for protection from insects. Accordingly, additional devices and methods are needed.

SUMMARY

Insect control devices and associated methods are generally described. The subject matter of the present invention involves, in some cases, interrelated products, alternative solutions to a particular problem, and/or a plurality of different uses of one or more systems and/or articles.

In one aspect, an insect control device is provided. The insect control device can comprise, in some embodiments, a hydrophobic material comprising a first insect control composition comprising a pyrethroid and a hydrophilic material comprising a second insect control composition comprising a pyrethroid and arranged adjacent the hydrophobic material.

In certain embodiments, the insect control device comprises a loaded substrate containing an active insect control species comprising a plurality of interstices containing a plurality of particles of the active insect control species having a first average particle size, and an outermost surface containing a plurality of particles of the active insect control species having a second average particle larger than the first average particle size.

In another aspect, a method for fabricating an insect control device is provided. The method can comprise, in some embodiments, contacting a substrate with a mixture comprising a pyrethroid, a fluid carrier, and an aqueous solution to produce a loaded substrate comprising the at least one pyrethroid.

In some embodiments, the method for fabricating an insect control device comprises contacting a substrate comprising a plurality of interstices with a mixture comprising particles of an active insect control species to produce a loaded substrate comprising the particles of the active insect control species, wherein the particles have an average particle size selected such that at least some of the particles enter a portion of the plurality of interstices upon contact with the substrate.

In certain embodiments, the method for fabricating an insect control device comprises contacting a substrate with a mixture comprising an active insect control species and a fluid carrier and removing the fluid carrier to produce a loaded substrate comprising the active insect control species, wherein the fluid carrier is selected to produce a loaded substrate having are release rate of the active insect control species of between about 1 milligram per hour and about 3 milligrams per hour.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
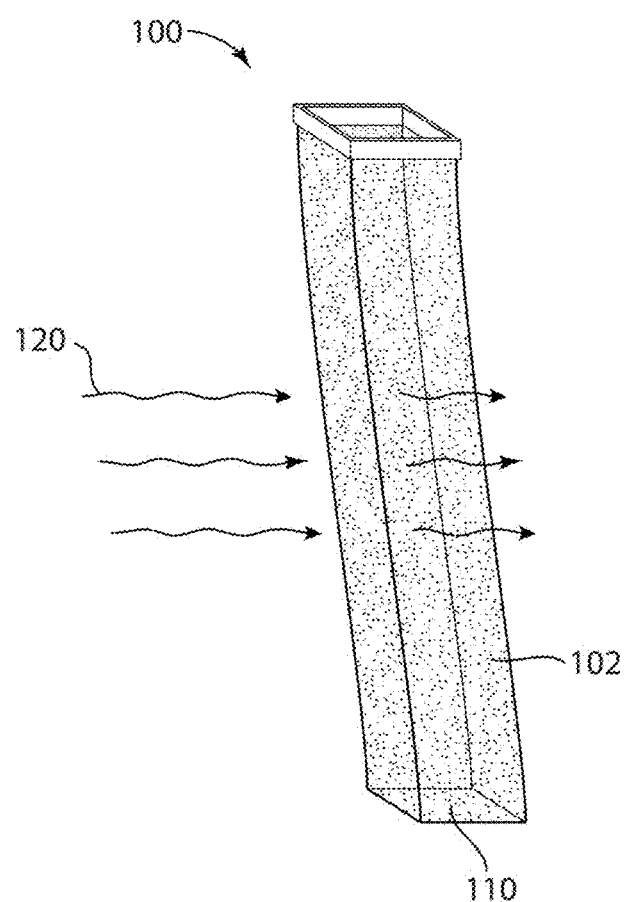
FIG. 1 shows an exemplary schematic of an insect control device, according to some embodiments.

Insect control devices and associated methods are generally described. Typically, the devices include one or more substrate materials impregnated or otherwise loaded with an active insecticidal species (e.g., a pyrethroid). In some cases, the device may provide protection against arthropods or other insects over prolonged periods of time. Such devices may be lightweight, low-cost, reusable, and disposable, and can be used for both indoor and outdoor purposes.

An advantageous feature of some embodiments described herein is the ability to release an active species (or combination of active species) without need for a source of external energy, such as heat, electricity, batteries, flame or the like (e.g., a "passive" device). In some cases, the device may be activated to release the active species by minimal airflow and/or ambient temperature. In some embodiments, the device may include one or more materials designed to release the active species at different release rates, such that the overall performance of the device is sustained or is substantially unchanged for long periods of time (e.g., three weeks or longer). For example, the device may include a first substrate capable of releasing an active species at a relatively faster rate, as well as a second substrate capable of releasing the same and/or different active species at a relatively slower rate. The release rate of the active species may be tailored by selection of the active species, substrate materials, and various fabrication conditions, as described more fully below.

In some embodiments, insect control devices are provided. Typically, the device may include a substrate or substrates loaded with one or more active species such as an active insect control/insecticidal species, where the substrate or substrates are provided in a sealed container. Use of the device may then, in some cases, involve unsealing the container to expose the loaded substrate(s) to the environment to be protected, upon which a vapor containing the active species is released. The device may protect the environment by, for example, repelling, knocking down, and/or killing insects such as arthropods (e.g., mosquitos) over a particular area. For example, a lid or other form of packaging may be removed from the sealed container to expose the loaded substrate(s) to the environment. In some cases, the loaded substrate(s) may be provided as a sheet in folded or rolled form, and may be unfolded or unrolled during use. The device may be, for example, hung or otherwise mounted on a surface, or may be a free-standing structure placed on a surface. Some embodiments may involve forming a quilt or pad from multiple layers loaded substrate, for example, to create a pad for outdoor protection. In other embodiments, the loaded substrate(s) are provided in the form of adhesive strips that can be worn by a user on clothing, shoes, or directly on the skin of the user. The term "user" generally refers to a person or animal wearing and/or otherwise utilizing the methods and/or devices described herein.

Generally, the active insect control ingredient may comprise at least one type of pyrethroid compound and, when released from the device, may repel, knock down, and/or kill arthropods (e.g., mosquitos) over a certain area. Pyrethroids are known in the art and include transfluthrin, tefluthrin, metofluthrin, allethrin, fenfluthrin, kadethrin, neopynamins, prallethrin, vapothrin, tefluthrin, esbiothrin, dichlovos (DDVP), and combinations thereof. It should be understood that other compounds with insect control/insecticidal properties may also be suitable for use in embodiments disclosed herein. In some embodiments, the pyrethroid may be loaded onto the substrates or materials as a layer, coating, powder, particle, or the like. It may be desirable in some embodiments for the device to include substrates or materials having different affinities for the active insect control species.

In some embodiments, the insect control device comprises a substrate attached to a base material. In some cases, the substrate may be loaded with the active insect control ingredient. FIG. 1 shows an exemplary illustration of an insect control device 100, which includes a substrate 102 attached to a base material 110. Substrate 102 may be loaded with a pyrethroid such as transfluthrin, and may be activated to release the pyrethroid as air flows through device 100 in a direction 120. The substrate (e.g., substrate 102) can generally comprise any number of suitable materials and may have any suitable construction. For example, the substrate be in the form of a woven, a non-woven, a knit, or an engineered fabric. In some embodiments, the fabric comprises one or more synthetic fibers. Substrates described herein may include a plurality of interstices or other interior spaces capable of containing the active insect control species. For example, the substrate include porous materials, fibrous materials, woven materials, web-like structures, or the like. In some such embodiments, the active insect control species may be present in the interstices/pores of the material.

Advantageously, the insect control device can be designed to be opened/deployed, releasing an active insect control species at a desirable release rate when opened/deployed, and subsequently closed, preventing the further release of the active insect control species and preserving the lifespan of the insect control device (e.g., by placing in a sealed container, and/or encasing in a small, thin, reusable shell or case). The insect control device may be configured for consumer use, comprising a carrier (e.g., a mesh carrier, a shell, a protective cover, a container, or the like), to prevent dermal contact/skin irritation. In some embodiments, the insect control device has an first (e.g., open/deployed) configuration and a second (e.g., closed) configuration. In certain embodiments, the insect control device may have a third (e.g., partially open/deployed) configuration. In some cases, a user may obtain or select between the first, second, and/or third configurations by, for example, expanding or compressing the substrate and/or base material.

Figure 2A:
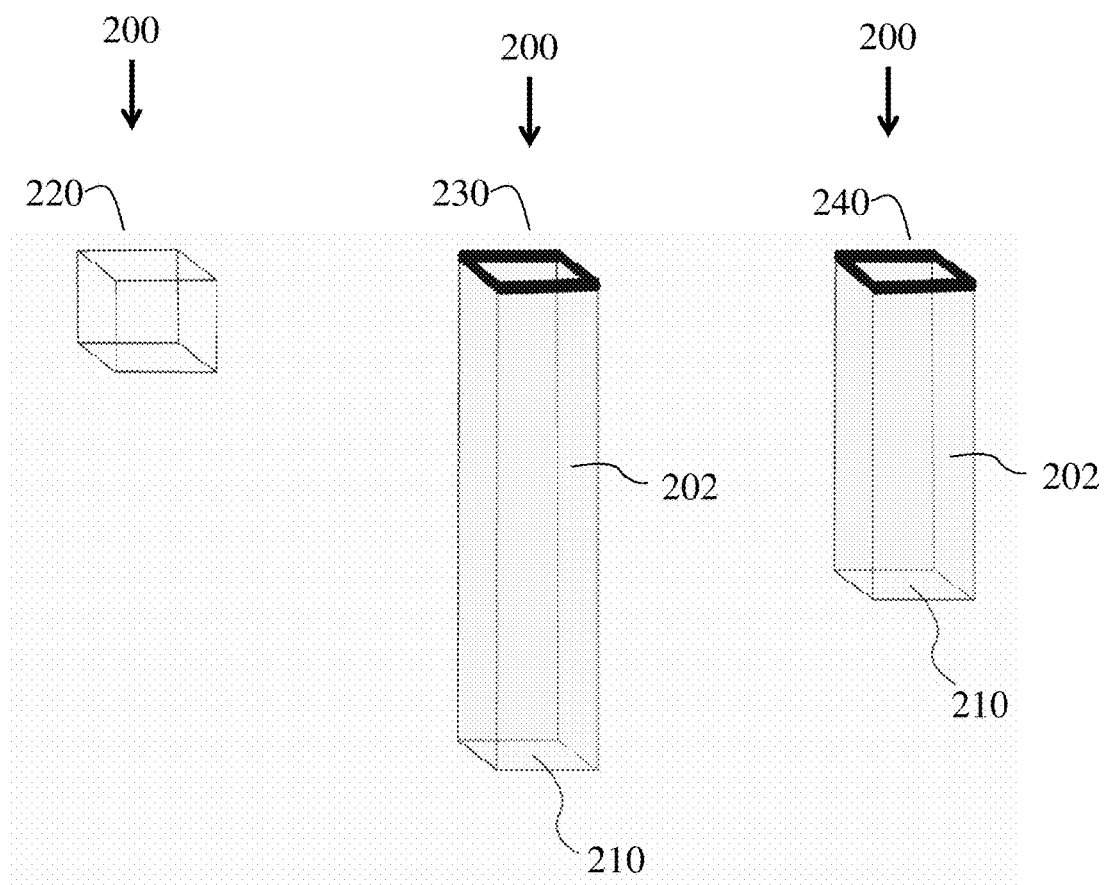
FIG. 2A shows exemplary schematics of an insect control device, according to some embodiments.
Figure 2B:
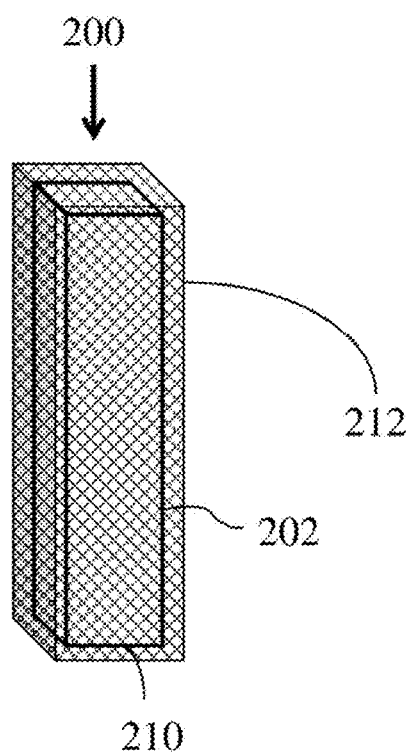
FIG. 2B shows the insect control device of FIG. 2A contained within a protective screen to prevent dermal contact of the user with the insect control agent containing substrate.

FIG. 2A shows an exemplary illustration of insect control device 200 in closed position 220, open/deployed position 230, and partially open/deployed position 240 comprising a substrate 202 and base material 210. FIG. 2B illustrates an exemplary embodiment of the insect control device of FIG. 2A arranged within a protective screen barrier/container 212 to prevent dermal contact of the user with the insect control agent containing substrate while facilitating air flow contact with the substrate. The protective screen barrier/container 212 may comprise any suitable material including, for example, mesh, fabric, metal, plastic, etc, such that the user does not substantially come in contact with the insect control agent when handling the device and/or permits contact of ambient air (e.g., air flow) with the substrate.

In some embodiments, the insect control device may be assembled by quilting multiple layers of treated substrates together, and then packaging or otherwise configuring the device for storage in an inactive state (e.g., in a sealed container) where the pyrethroid is not released to an open space or environment. The quilted layers of treated substrates can be opened, assembled, if needed, and placed in a desired location to repel and/or kill insects. In some embodiments, the insect control device is arranged in combination with a self-adhesive strip for attachment to clothing and apparel (e.g., shirts, pants, boots, backpacks, duffel bags, footwear, and the like), to the body (e.g., patches for the arms and/or legs), and/or to surfaces (e.g., ceilings and/or beams of tents, temporary structures, or permanent structures). As noted herein, in certain embodiments, the active insect control species may be released and/or exposed, and release of the vapor containing the pyrethroid may be activated by airflow and/or ambient heat. In some embodiments, active insect control species may be released and/or exposed and release of the vapor containing the pyrethroid may be activated by relatively minimal airflow.

In certain embodiments, the insect control device is free-standing. For example, in some embodiments, the insect control device may be configured to be placed on a shelf, a table, and/or a floor. Advantageously, the design of the insect control device, as described herein, can allow in certain cases for the insect control device to be easily scaled to address the need of a particular environment (e.g., indoors vs. outdoors) as compared to existing insect control devices which require sources of power and/or have limited flexibility for product dimensions and are mainly for outdoor use. In some embodiments, the insect control device ranges in size from 4 in.×4 in.×4 in. to 10 in.×10 in.×6 in., or larger. For example, in certain embodiments, the insect control device has at least one dimension (e.g., length, width, and/or height) of at least about 4 inches, at least about 6 inches, at least about 8 inches, or at least about 10 inches. In some embodiments, the insect control device has at least one dimension less than or equal to about 12 inches, less than or equal to about 10 inches, less than or equal to about 8 inches, or less than or equal to about 6 inches. Combinations of the above-referenced ranges are also possible (e.g., a length, width, and/or height of between about 4 inches and about 10 inches or between about 6 inches and about 10 inches). Other ranges are also possible.

As noted herein, the insect control device may include one or more substrate materials. In some embodiments, the insect control device comprises one or more hydrophobic materials. In some embodiments, the insect control device comprises one or more hydrophilic materials. Non-limiting examples of hydrophobic materials include glass (e.g., comprising glass fibers), plastic or other synthetic materials (e.g. synthetic or plastic films). Suitable glass fiber materials may include, for example, St. Gobain FibaFuse™. In certain embodiments, the insect control device comprises one or more hydrophilic materials. Non-limiting examples of hydrophilic materials include natural cellulosic materials (e.g., cellulose fibers and/or cotton fibers), synthetic cellulosic materials, combinations of natural and cellulosic materials, and filter paper. Suitable cellulosic materials may include, for example, Ahlstrom Grade 1278 or Evolon® fabrics. Other materials and combinations of materials may also be possible. In one embodiment, the substrate includes a glass fiber material arranged in contact with a cellulose material.

In some cases, the device may include a hydrophobic material and a hydrophilic material configured and arranged such that the hydrophilic material is adjacent the hydrophobic material. In certain embodiments, the hydrophilic material is in direct contact (e.g., directly adjacent, in physical contact) with the hydrophobic material. The hydrophilic material and hydrophobic material may be arranged, for example, as layers in a multi-layer stack, as rolled layers within a cylindrical structure, or the like. The hydrophilic material and/or the hydrophobic material may be loaded (e.g., coated, impregnated, etc.) with one or more insect control species (e.g., at least one type of pyrethroid). In some cases, the hydrophilic material and the hydrophobic material are separately loaded with an active insect control species, and then assembled to form the device. In some cases, the hydrophilic material and the hydrophobic material are first assembled to form a combined substrate, which is then the loaded with an active insect control species. In some cases, the hydrophilic and hydrophobic materials may exhibit similar release rates for the active insect control species. In some cases, the hydrophilic and hydrophobic materials may exhibit different release rates for the active insect control species.

In some embodiments, the hydrophobic material comprises a first insect control species (e.g., a first composition comprising a pyrethroid) and the hydrophilic material comprises a second insect control species (e.g., a second composition comprising a pyrethroid). The first composition comprising a pyrethroid and the second composition comprising a pyrethroid may comprise the same pyrethroid compound as an insect control species, or, in some cases, may comprise different pyrethroid compounds. During use, the device may release the pyrethroid, or other active species, at one or more desired release rates. In some embodiments, during use, the pyrethroid may be released at a slower rate from the hydrophobic material than the same and/or other pyrethroid is released from the hydrophilic material. In some embodiments, during use, the pyrethroid may be released at a faster rate from the hydrophobic material than same and/or different pyrethroid is released from the hydrophilic material.

In some cases, release rates of the pyrethroids may range between about 0.1 milligrams per hour and about 3 milligrams per hour, as measured by gas chromatography mass spectroscopy (GC-MS). In some embodiments, the release rate may range between about 0.1 milligrams per hour and about 3 milligrams per hour, between about 0.5 milligrams per hour and about 3 milligrams per hour, or between about 1 milligrams per hour and about 3 milligrams per hour for an overall device of the invention, as measured by GC-MS. Other release rates are also possible. The release rate of the pyrethroid may be determined, for example, by immersing a loaded substrate in a suitable solvent (e.g., acetone) and sonicating. The substrate may then be rinsed and the solvent containing the released pyrethroid is collected. Analysis of the solvent containing the released pyrethroid by GC-MS at varying temperatures over time can provide the relevant information to determine release rate, as demonstrated in the Examples below. Release rates may be expressed in milligrams per hour.

The hydrophilic and/or hydrophobic material may be selected to have a particular desired thickness. In some embodiments, the thickness of the hydrophilic material and/or the hydrophobic material ranges between about 1 micron and about 2000 microns, between about 1 micron and about 1000 microns, or between about 1 micron and about 500 microns. Other thicknesses are also possible.

In certain embodiments, the hydrophilic material and/or the hydrophobic material may have a particular basis weight. In some embodiments, the basis weight ranges between about 1 lbs/100 ft$^2$ and about 5 lbs/100 ft$^2$, between about 0.5 lbs/100 ft$^2$ and about 4 lbs/100 ft$^2$, or between about 0.5 lbs/100 ft$^2$ and about 2 lbs/100 ft$^2$. Other basis weights are also possible.

Methods for fabricating an insect control device are also provided. The methods in certain embodiments comprise contacting the active insect control species with the substrate. In some embodiments, the active insect control species is contacted with the substrate in dry form (e.g., as a powder). In certain embodiments, the active insect control species is contacted with the substrate in vapor, aerosol and/or liquid form (e.g., as a solution comprising the active insect control species). The methods may involve loading a substrate with the active insect control species using various dry processes (e.g., spraying), wet processes (e.g., wet-dipping), or combinations thereof. In some embodiments, the active insect control species may be dispersed or dissolved in a fluid carrier (e.g., a solvent) and/or an aqueous phase (e.g., water) to form a mixture, which is then placed into contact with the substrate. In certain embodiments, the active insect control species may be sprayed onto the substrate in particulate/suspension form. The loaded substrate may then be further processed to produce the device. For example, the loaded substrate may be coated with additional materials, annealed, and/or arranged in combination with other components, such as a container. In some cases, the loaded substrate is contained/stored/shipped within a sealed container.

Methods disclosed herein involve the selection of various materials, fabrication processes, conditions, and/or other components to produce a device having a particular release rate, or set of release rates, of the active insect control species. For example, the release rate can be selected, as described herein, such that the insect control device remains effective (e.g., in the knock-down, repulsion, and/or killing of arthropod insects) for greater than 1 day, greater than 7 days, greater than 21 days, or greater than 30 days. In some cases, the selection of such parameters may be made based on the vapor pressure of the active insect control species (e.g., a pyrethroid), or other active species.

In certain embodiments, the active insect control species has a particular vapor pressure (e.g., such that the active insect control species is released when in contact with air). In some embodiments, the vapor pressure of the pyrethroid, or other active insect control species is between about $1\times10^{-4}$ and about $10\times10^{-4}$ Pascals at 20° C. In certain embodiments, the vapor pressure of the active insect control species is at least about $1\times10^{-4}$, at least about $2\times10^{-4}$, at least about $4\times10^{-4}$, at least about $6\times10^{-4}$, at least about $8\times10^{-4}$, or at least about $9\times10^{-4}$. Other vapor pressures may also be possible.

In some embodiments, the methods may comprise the use of one or more forms of chemical treatment/application of chemical energy, such as selection of a chemical reagent, or application of physical energy, or other selection and/or manipulation of materials and/or processing conditions, that may be applied to the substrate(s) prior to, during, and/or subsequent to application of the active insect control species. Such forms of chemical/physical energy/treatments may be used to accelerate or inhibit the release of the active insect control species from the substrate during use. In some cases, devices may be fabricated and designed so that the active insect control species may be substantially depleted from the substrate over a specified time interval such that, after use, the device may be safely disposed of, thereby reducing environmental risks associated with insecticide disposal. For example, one or more sources of chemical energy and/or application of chemical agents may be used to modulate vapor pressure, release rate, etc., of the active insect control species. Exemplary treatments/agents/etc. are discussed in more detail below and in the examples. In each case, the effect and desirability of such treatment may be determined based on screening tests on the fabricated product to determine the release rate(s) of the active insect control ingredient(s). Those skilled in the art would be capable of selecting suitable screening tests based on the teachings of this specification.

For example, in some embodiments, the average particle size of the active insect control species loaded into/onto the substrate(s) may be selected to produce a device having a particular release rate, or set of release rates. In some cases, the method may involve contacting a substrate comprising a plurality of interstices (e.g., space between fibers, space between materials, and/or pores) with a mixture comprising particles of the active insect control species to produce a loaded substrate comprising particles of the active insect control species. In some embodiments, at least some of the particles may be selected to have a sufficiently small average particle size such that the particles enter (e.g., are loaded into) at least some of the interstices of the substrate. In some such cases, the release rate of such particles may be relatively slower (e.g., as compared to particles not present in the interstices of the substrate). In some embodiments, at least some of the particles may selected to have a sufficiently large average particle size such that the particles are coated onto an outermost/exterior surface of the substrate rather than entering the interstices of the substrate. In such cases, the release rate of such particles may be relatively faster, (e.g., as compared to the release rate of particles present in the interstices of the substrate). In some cases, a plurality of particles having a relatively small average particle size may be loaded into the interstices of a first substrate, and a plurality of particles having a relatively large particle size may be loaded onto an outermost surface of a second substrate. In some such embodiments, the first and second substrate may be arranged in combination (e.g., in contact, as described above). In some cases, a set of particles having a relatively small average particle size and a set of particles having a relatively large particle size may be loaded onto a single substrate, producing a substrate having a first plurality of particles contained within interstices and a second plurality of particles positioned (e.g., disposed on, in contact with, and/or adjacent) on an outermost surface of the substrate, thus resulting in at least two different release rates of the pyrethroid.

As an illustrative embodiment, an engineered web, such as a web with a honeycomb structure, may be coated with finer particles comprising a pyrethroid which may collect within the interstices of the web, thereby producing a relatively slower release rate. By contrast, application of larger particles or a broader-size distribution of particles (e.g, with particles having an average particle size exceeding an average pore size of the outermost surface of the substrate) on such web, or of particles or non-particulate active species on a non-absorbent/non-porous web/substrate may produce a relatively faster release rate. A screening test for determining the appropriate average particle size for use in a particular application may involve the coating of pyrethroid particles of various average particle sizes or various particle size distributions to a substrate to produce a series of loaded substrates. Evaluation of the release rates of each loaded substrate may then, in some cases, determine the appropriate average particle size or average particle size distribution for use in a particular application with a given substrate.

In some cases, the active insect control species (e.g., pyrethroid) in particle form has an average particle size between about 1 micron and about 1000 microns, between about 1 micron and about 900 microns, between about 1 micron and about 800 microns, between about 1 micron and about 700 microns, between about 1 micron and about 600 microns, between about 1 micron and about 500 microns, between about 1 micron and about 400 microns, between about 1 micron and about 300 microns, between about 2.5 microns and about 300 microns, between about 2.5 and about 200 microns, between about 2.5 and about 100 microns, or between about 2.5 and about 30 microns. Average particle size as used herein generally refers to the median (D50) diameter of the particles and is determined by dynamic light scattering, for example using a Malvern Particle Size Analyzer. Dynamic light scattering techniques will be generally known to those skilled in the art. Other ranges of the average diameter of a particle are also possible. In some embodiments, the release rate may be increased by selecting a smaller average particle size or decreased by selecting a larger average particle size.

In some embodiments, the substrate material (e.g., hydrophilic material, hydrophobic material, or combinations thereof) may be selected to have surface energy/wettability properties that impart a particular release rate of an active insect control species for a given species in a given carrier composition. For example, certain substrate properties may allow for control over the release and evaporation rates of a pyrethroid, or other active species. In some cases, the substrate may be selected to have a particular affinity for the active insect control species. In some cases, the substrate may be selected to absorb or adsorb the active insect control species to a particular desired extent. For example, the substrate material may be selected to absorb the active insect control species such that the active insect control species becomes physically trapped between multiple layers and/or different sized fibers of the substrate. In some embodiments, the substrate material may be selected to adsorb the active insect control species onto an outermost/exterior surface of the substrate, allowing the active insect control species to evaporate readily.

The substrate material may be selected to have pores or interstices of a particular size, density, and or shape. For example, the substrate may be selected to be capable of being loaded with a sufficient amount of active insect control species, while also being capable of allowing sufficient amount of air to flow through the substrate. In some embodiments, the size of the pores/interstices of the substrate may be greater than an average particle size of the active insect control species. In certain embodiments, the size of the pores/interstices of the substrate may be less than an average particle size of the active insect control species.

Those skilled in the art would be capable of conducting screening tests for determining the appropriate substrate material for use in a particular application, based upon the teachings of this specification. For example, a series of different substrates may be coated with particles of active insect control species having a certain average particle size or particle size distribution to produce a series of loaded substrates. Evaluation of the release rates of each loaded substrate may then determine the appropriate substrate material for use in a particular application.

In some embodiments, the selection of the fluid carrier used during the fabrication process may affect the resulting release rate of the active insect control species. For example, during fabrication, the fluid carrier may be combined with the active insect control species to produce particles of a certain average particle size (e.g., particle size can affect the release rate of the device, as described above). In some cases, the fluid carrier may partially or completely dissolve the active insect control species, which, when applied to the substrate, may result in controlled and relatively consistent release rate of the active insect control species during use. In some embodiments, the active insect control species may be evenly dispersed within the fluid carrier such that, when applied to the substrate, the active insect control species has a controlled and relatively consistent release rate. Those skilled in the art would understand that consistent release rate does not refer to an exact release rate, but instead generally refers to a release rate that does not significantly deviate (e.g., more than about 5%, more than about 10%, or more than about 20%) from an average release rate.

Suitable (or potentially suitable) solvents may depend on the particular insect control species employed. Non-limiting examples of suitable solvents for pyrethroid compounds include organic solvents, such as acetone, benzene, p-cresol, toluene, xylene, diethyl ether, glycol monomethyl or dimethyl ether, petroleum ether, hexane, cyclohexane, methylene chloride, chloroform, carbon tetrachloride, dioxane, tetrahydrofuran (THF), dimethyl sulfoxide, dimethylformamide, N-methyl-2-pyrrolidone, hexamethyl-phosphoric triamide, ethyl acetate, pyridine, triethylamine, picoline, mixtures thereof, or the like. In certain embodiments, the solvent is a polar aprotic solvent (e.g., propylene carbonate, dimethylformamide, N-methyl-2-pyrrolidone).

In some cases, the fluid carrier may be characterized by and selected based upon its boiling point. For example, the fluid carrier may be selected to have a boiling point such that the release rate of the active insect control species from the loaded substrate is accelerated (e.g., as compared to the active insect control species alone). In other cases, the fluid carrier may be selected to decrease the release rate of the active insect control species from the loaded substrate (e.g., the fluid carrier having a boiling point such that the release rate is decreased as compared to the active insect control species alone). In some embodiments, the fluid carrier may be selected to produce particles of active insect control species having a particular size, which in turn can affect the resulting release rate of the device. In some embodiments, the fluid carrier may be a relatively volatile fluid carrier. A simple screening test for selection of the appropriate fluid carrier may include applying mixtures containing a pyrethroid, or other desired active insect control species, in a series of fluid carriers to the desired substrate(s), and evaluating the release rate of the loaded substrates using methods disclosed herein.

It may be advantageous, in some embodiments, to select a combination of one or more of a fluid carrier, a substrate, an average particle size, and a method of fabrication, as described herein, to produce an optimal release rate for the active insect control species. For example, in some cases, a desired release rate may be achieved by choosing an appropriate combination of solvents (e.g., to produce a particular average particle size) and substrates with a particular method of fabrication. Routine screening tests and optimization experimentation for selection of the appropriate combinations may include applying a pyrethroid, or other active species, mixed with a fluid carrier to a substrate via a selected method of fabrication and evaluating the release rate of the substrate. In some cases, the average particle size of the active insect control species, fluid carriers, and/or substrate materials are selected, in combination, such that substantially all of the active insect control species is released from the substrate over a certain period of time. In some embodiments, substantially all of the active insect control species is released from the substrate in at least 1 day, in at least 7 days, in at least 14 days, in at least 21 days, or in at least 30 days. In certain embodiments, the pyrethroid is released from the substrate at a different rate on the first day as compared to after 7 days, after 14 days, after 21 days, and/or after 30 days. That is to say, after a certain period of time, less than about 10 wt %, less than about 5 wt %, less than about 2 wt %, or less than about 1 wt % of the pyrethroid (or other active insect control species) is present on the substrate as compared to the active insect control species initially loaded onto the substrate.

In some cases, the plurality of particles may be selected such that at least 50% of the particles of the active insect control species from the mixture that is contacted with the substrate are arranged within some of the interstices of the substrate. In certain embodiments, at least 10%, at least 25%, at least 50%, at least 75%, or at least 90% of the particles of the active insect control species (e.g., a pyrethroid particle) from the mixture are arranged within some of the interstices of the substrate. As noted herein, the process of controlling particle size may also be facilitated by solvent selection and solution treatments/sonication. In some cases, the average particle size of a pyrethroid particle can be controlled (e.g., increased or decreased) by mixing the pyrethroid particle (e.g., via ultrasonic mixing or via a homogenizer) in a suitable solvent (e.g., acetone or hexane).

In some embodiments, the insect control device is fabricated by contacting a substrate (e.g., a substrate material) with a mixture comprising an active insect control species (e.g., pyrethroid), a fluid carrier, and an aqueous solution thereby producing a loaded substrate comprising the at least one active insect control species. In some embodiments, the method (e.g., for fabricating the device) comprises contacting a first substrate with a first mixture comprising a pyrethroid (or other active insect control species), a fluid carrier, and an aqueous solution thereby producing a loaded substrate comprising the pyrethroid. A second substrate may be contacted with the same or a different mixture comprising the same and/or different pyrethroid (or other active insect control species), a fluid carrier, and an aqueous solution thereby producing a second loaded substrate comprising a pyrethroid. The first substrate may be assembled with the second substrate for form the insect control device. Alternatively, the method may involve first arranging a first substrate (e.g., a hydrophobic material) and a second substrate (e.g., a hydrophilic material) together to produce a combined substrate, and then contacting the combined substrate with a mixture containing the pyrethroid(s) (or other active insect control species). Methods disclosed herein may involve loading more than one type of pyrethroid, or other active insect control species, onto a substrate, either simultaneously or sequentially.

The active insect control species may be combined with a fluid carrier (e.g., solvent) prior to coating the substrate to form a mixture containing the active insect control species. In some embodiments, the mixture may include water or an aqueous solution that may be mixed with the active insect control species using various methods known in the art (e.g., sonication) prior to loading onto a substrate. In some cases, the mixture may be formulated and/or mixed (e.g. via sonication and/or homogenization) to optimize (e.g., decrease) the average particle size and/or distribution of particles sizes of the active insect control species prior to loading onto a substrate. The mixture may comprise additional agents to control the absorbency of an active insect control species into/onto a substrate, and/or to increase or decrease the release rate of an active insect control species from a substrate. In some cases, the mixture comprises a surfactant. Suitable surfactants are known in the art.

In some embodiments, the substrate including a plurality of interstices may be contacted with the mixture, followed by removal (e.g., drying) of any fluid carrier, aqueous solution, or other wet component from the substrate, to produce a loaded substrate comprising the particles of the active insect control species. In some embodiments, the coated substrates may be dried using a heat source (e.g., hot air, microwave, an infrared source, or other sources of energy), via contact drying (e.g., running the substrate over a hot surface), or through evaporation (e.g., air drying).

The step of contacting may involve dipping, soaking, or otherwise immersing the substrate in the mixture (e.g., via a wet application/process). In certain embodiments, the substrate may be in roll form (e.g., single ply). In some embodiments, the method may involve spraying the mixture and/or spraying the active insect control species in substantially dry form onto the substrate. Excess mixture may be removed, in some embodiments, by mechanical methods (e.g., squeezing via nip rolls) to produce substrates with desired level of insect control species loading. This may be determined by measuring the weights of the substrate prior to and following loading.

Any of the processes described herein may be conducted at a relatively small scale (e.g., comprising one or several devices), at a moderate scale (e.g., comprising a plurality of devices), or in large vats.

In some embodiments, the method may further involve formation of an adhesive material on the loaded substrate (e.g., a hydrophilic material, a hydrophobic material). In some cases, more than one adhesive material may be formed on the loaded substrate. It may be advantageous, in some cases, to coat a hydrophobic material and/or hydrophilic substrate material(s) with an adhesive to impart different release rates as compared to substrate materials lacking an adhesive. In some embodiments, the adhesive material may allow for the attachment of additional pyrethroid particles to the surface of the loaded substrate. Non-limiting examples of potentially suitable adhesives include acrylate, polyvinyl acetate, polyvinyl alcohol, polyvinylpyrrolidone, silicone latex, cyanoacrylate, epoxy, and polyurethane adhesives. In some embodiments, the active insect control species is adhered to the substrate by the adhesive. In certain embodiments, at least a portion of the active insect control species may be at least partially embedded within the adhesive.

In some embodiments, the active insect control species may be reconstituted prior to coating. For example, the active insect control species may be dissolved in a solvent and then the solvent evaporated, producing a dried insect control species which can then be ground and sifted onto a substrate. In some embodiments, the reconstituted insect control species may be attached to the substrate (e.g., via a dry application/process) before and/or after the step of contacting, as described herein. For example, a loaded substrate may be coated with an adhesive material (e.g., an acrylate adhesive), and the reconstituted insect control species may be attached to the adhesive material. In some cases, the reconstituted insect control species may be combined with an adhesive material and the mixture may be applied to the surface of a substrate and/or loaded into a substrate and/or applied to the surface of a previously insect control agent loaded substrate.

In some cases, the substrate may be selected to comprise a flexible material. In some cases, the loaded substrate may be mechanically flexible allowing for further modification or processing. In certain embodiments, the coated substrate may be rolled for further treatment and downstream processing. An exemplary method of fabrication of an insect control device is described in Example 4. The device may be rendered and/or packaged to be in an inactivated state prior to use. For example, the device may be rolled, folded, or otherwise rendered in an inactivated state and/or may be placed in a sealed container or other packaging. In some cases, the substrate is placed in a sealed container and shrink-wrapped for consumer use.

The insect control device may be activated by removing any protecting packaging (e.g., shrink-wrap, self-adhesive strip cover, etc.) and/or placing the device in a desired location. In some cases, the insect control device may be activated by opening a container (e.g., a shell or a case). Any packaging or container containing an insect control device may also be closed when not in use to prevent further release of the pyrethroid or other active species. The device may then be re-opened for subsequent use.

EXAMPLES

Example 1: Transfluthrin Evaporation

Figure 3A:
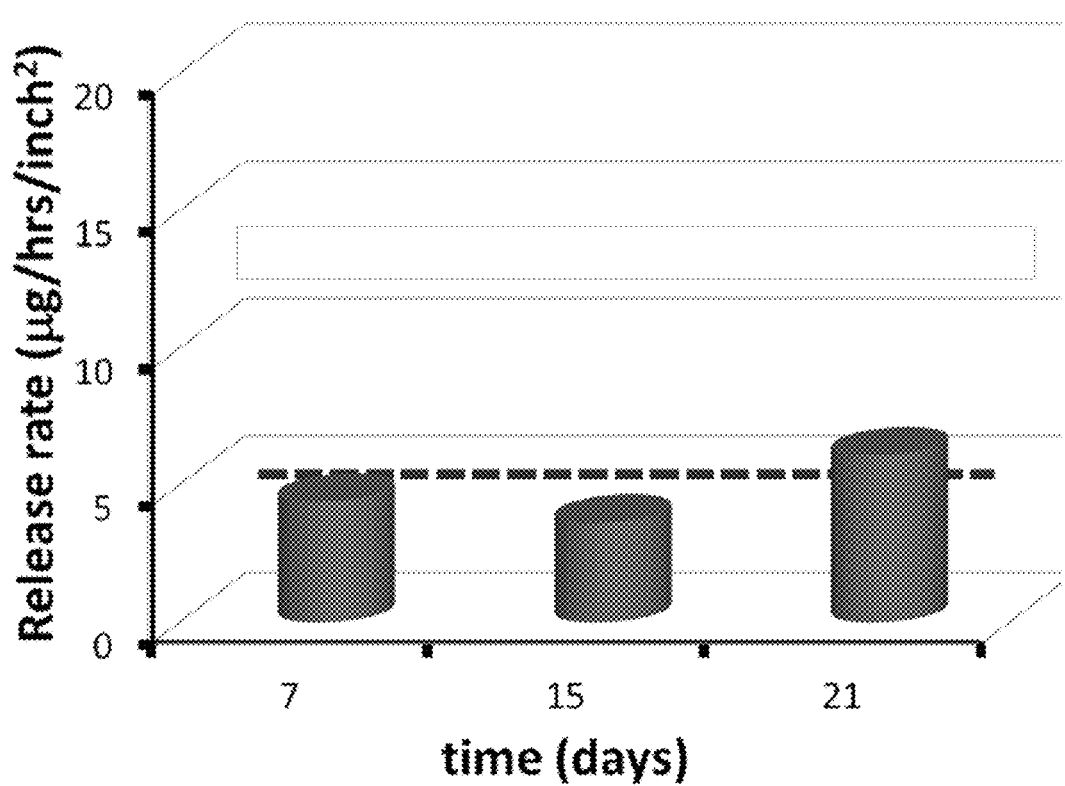
FIGS. 3A-3F show plots of release rate data from the specific embodiment described in Example 1 for (3A) a cellulose-based substrate loaded with an active insect control ingredient via a wet process, (3B) a cellulose-based substrate loaded with an active insect control ingredient via a wet and dry process, (3C) a glass-based substrate loaded with an active insect control ingredient via a wet process, (3D) a glass-based substrate loaded with an active insect control ingredient via a wet and dry process, (3E) a cellulose-based substrate loaded with an active insect control ingredient via a wet process, (3F) and a cellulose-based substrate loaded with an active insect control ingredient via a wet and dry process for loading/coating a substrate with a pyrethroid, according to some embodiments.
Figure 3B:
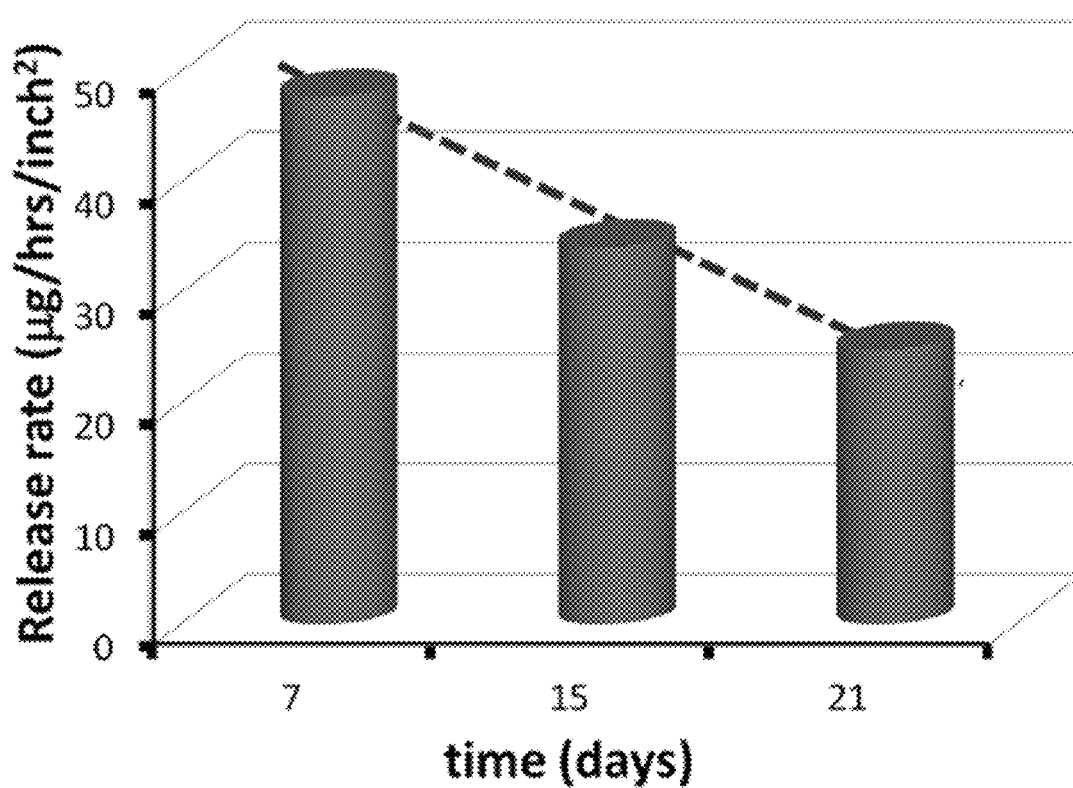
Figure 3C:
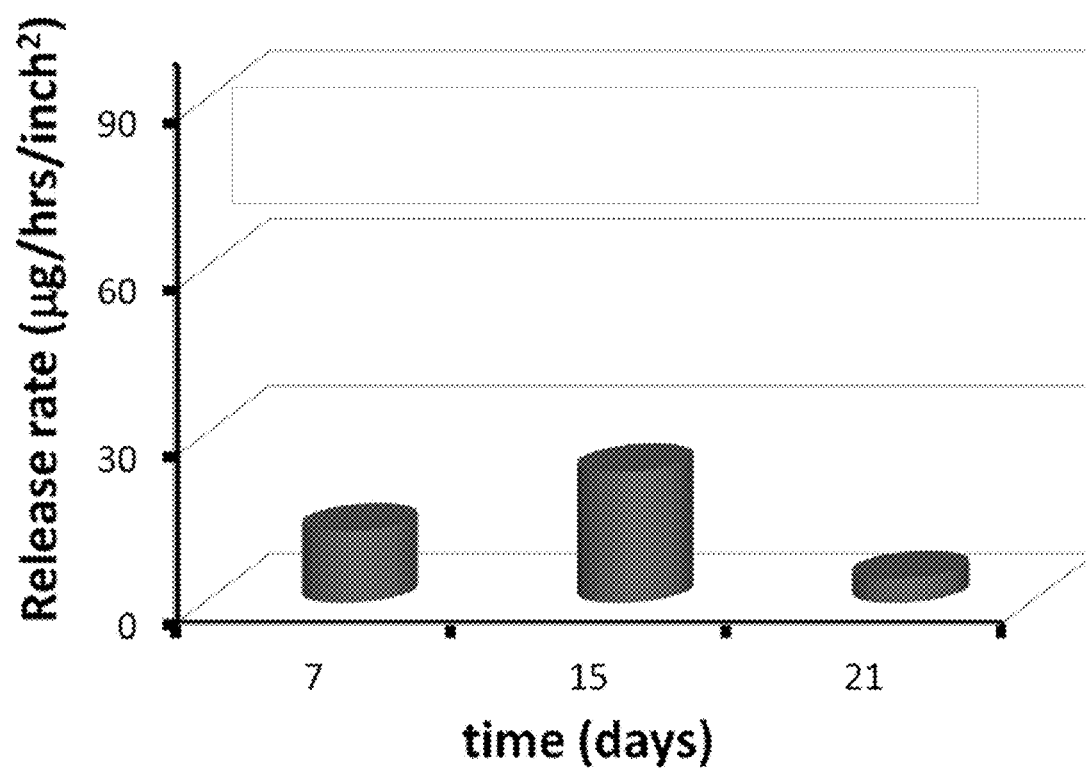
Figure 3D:
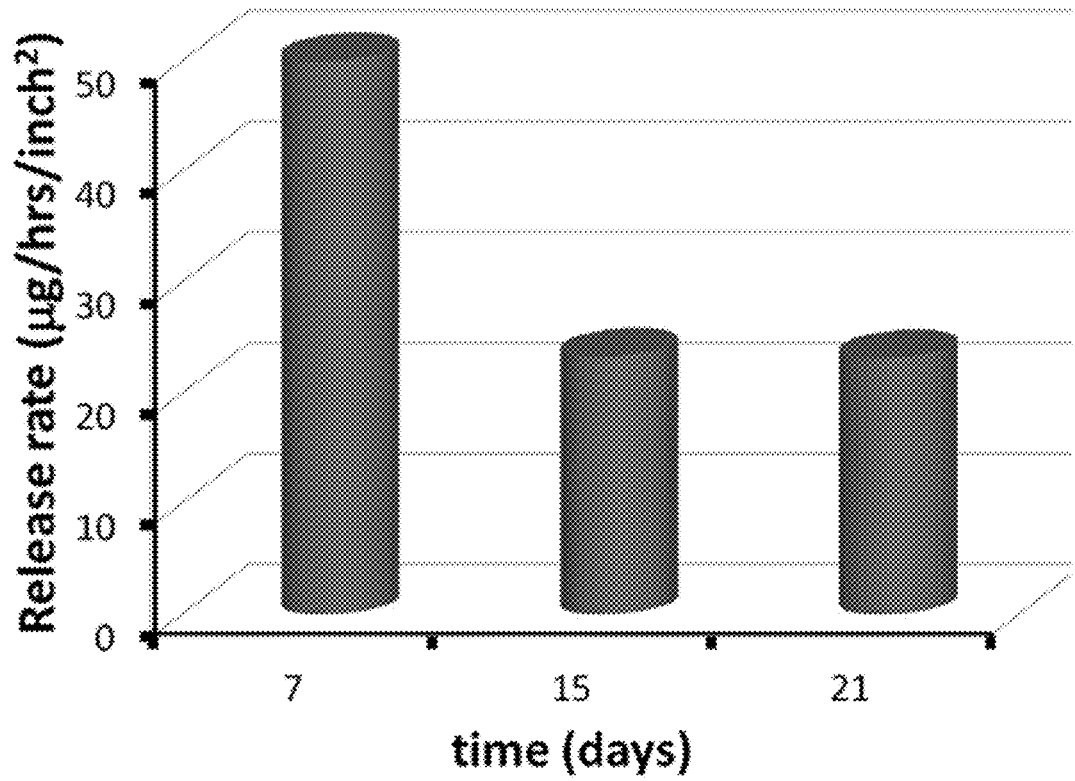
Figure 3E:
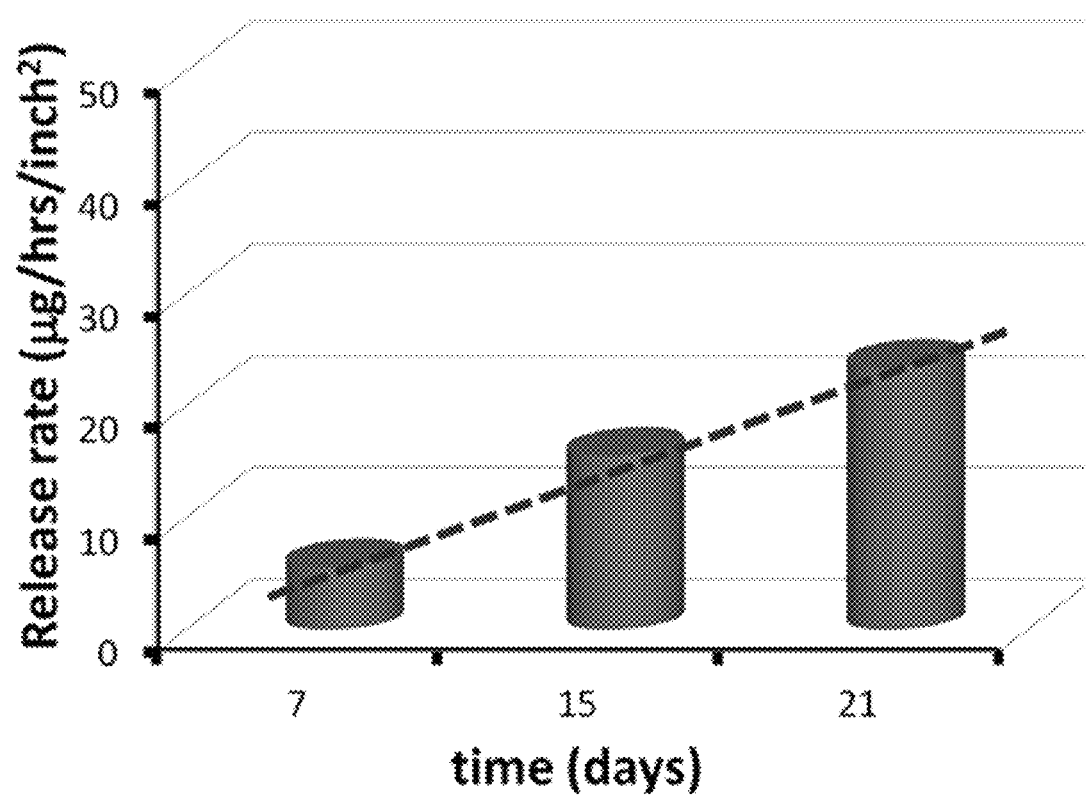
Figure 3F:
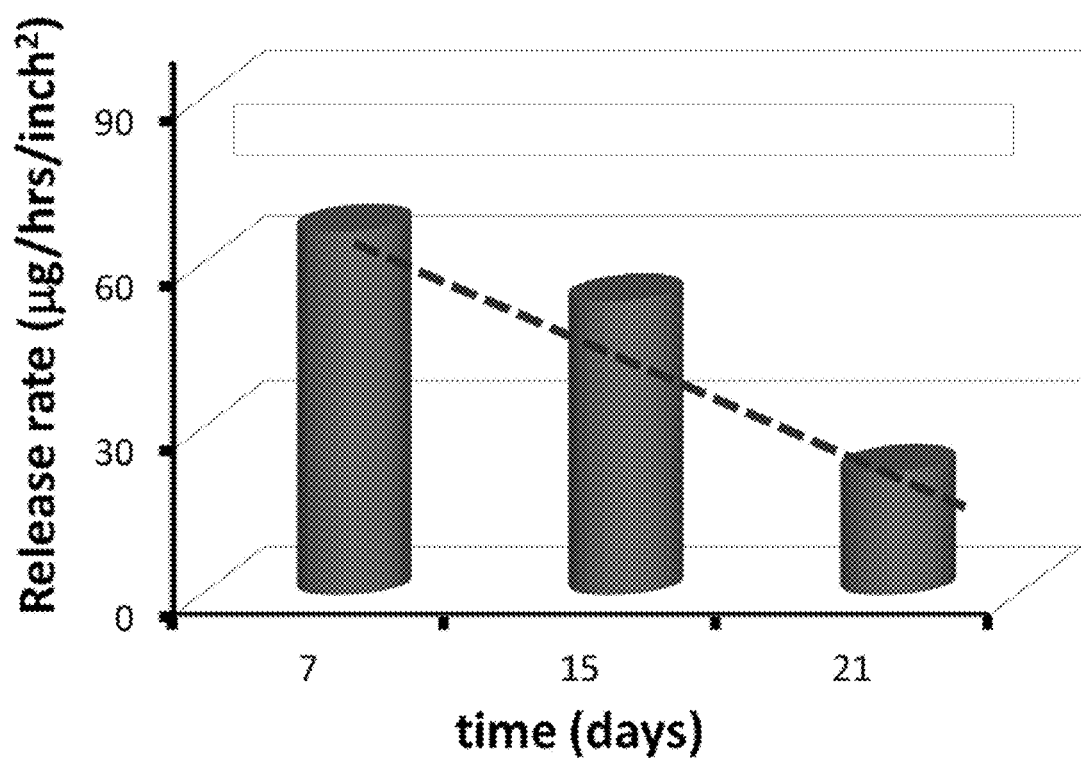

Fabric samples comprised of cellulose or glass were prepared with Transfluthrin using either a wet application, or a wet application followed by a dry application, as described herein. Weight change after the addition of Transfluthrin is detailed in Table 1. Fabric samples were aged at 70° F. and 70% relative humidity in a climate controlled chamber. Samples were removed at 7 day intervals and placed in a 100 mL beaker. 30 mL of acetone was added and the beaker was placed on a sonicator bath for 10 minutes. The contents were transferred to a volumetric flask and the fabric was rinsed thoroughly with acetone. Up to 50 mL of acetone was collected. The amount of Transfluthrin in the extracted sample was measured using a Restel Rtx®-5MS gas chromatography—mass spectrometry column. 1 Microliter samples were injected in a split mode at a 45:1 ratio and at 240° C. Samples were then heated to 150° C. and held for 2 minutes, ramped at 10° C. per minute to 300° C. and held for 3 minutes, and then ramped at 10° C. per minute to 330° C. Mass spectrometry was acquired at from 35 to 450 mass-to-charge ratio. Measured release rates for various substrates and preparation methods are summarized in Table 2. Evaporation rates, as determined by solvent extraction of Transfluthrin and followed by GC-MS as described previously, for cellulose fabric wet application and wet-and-dry application samples (Samples A and B in Table 1) are plotted in FIG. 3A and FIG. 3B, respectively. Evaporation rates for glass fabric wet application and wet-and-dry application samples (Samples C and D in Table 1) are plotted in FIG. 3C and FIG. 3D, respectively. Evaporation rates for cellulose fabric wet application and wet-and-dry application samples (Samples E and F in Table 1) are plotted in FIG. 3E and FIG. 3F, respectively.

Transfluthrin evaporated from cellulose-based textiles more uniformly whereas transfluthrin coated on glass-fiber substrates evaporated rapidly in short term. The larger transfluthrin particles appeared to evaporate more quickly than smaller transfluthrin particles. Without wishing being bound to theory, it is believed the smaller transfluthrin particles were entrapped in the fabric interstices, leading to the lower rate of evaporation. For example, a combination of particle size distributions of transfluthrin deposited on a 5"×4" square fabric of cellulose evaporated at a rate of 0.5 mg per 21 days (i.e., 10 mg per 21 days on an equivalent 20"×20" cellulose fabric). As a comparative example, conventional liquid emanatory devices (e.g., insect control devices which require heat, air flow, and/or electricity to release transfluthrin and other vapor-active compounds) typically exhibit release rates between about 1 mg/hr and about 2 mg/hr.

TABLE 1

Weight change of substrates after the addition of transfluthrin (TF).

| Sample # | Substrate | Untreated | After wet | After 24 hr. drying | Gain | After binder | TF added | Notes |
|---|---|---|---|---|---|---|---|---|
| A | Cellulose | 1.04 | 6.52 | 2.22 | 1.18 | N/A | N/A | Only treated with dissolved TF |
| B | Cellulose | 1.03 | 6.32 | 2.32 | 1.29 | 3 | 0.75 | Treated with wet and dry TF |
| C | Glass | 0.74 | 5.68 | 1.57 | 0.83 | N/A | N/A | Only treated with dissolved TF |
| D | Glass | 0.7 | 5.5 | 1.63 | 0.93 | 2.1 | 0.75 | Treated with wet and dry TF |
| E | Cellulose | 1.25 | 8.37 | 2.81 | 1.56 | N/A | N/A | Only treated with dissolved TF |
| F | Cellulose | 1.25 | 8.66 | 3.1 | 1.85 | 3.6 | 0.75 | Treated with wet and dry TF |

TABLE 2

Release rates of substrates loaded with transfluthrin.

| ID | Amount (mg/mL) From GC results | Weight of sample (in g) | Sample extracted in acetone (mL) | Measured sample area (inch$^2$) | TF in mg per inch$^2$ of substrate | Δ (mg/inch$^2$) | Duration (days) | Release rate of Transflutrhrin μg/inch$^2$hrs) | Total amount of TF (g) for 5 × 4 inch$^2$ substrate | Release of TF mg/hrs from 5 × 4 inch$^2$ substrate | Total amount of TF in grams for 5 × 4 inch$^2$ |
|---|---|---|---|---|---|---|---|---|---|---|---|
| | | | | | | 0 day | | | | | |
| A | 2.62 | 0.2557 | 50 | 2.476 | 52.905 | 0.00 | 0 | | 1.06 | | 1.18 |
| B | 1.56 | 0.1270 | 50 | 0.922 | 84.635 | 0.00 | 0 | | 1.69 | | 2.04 |
| C | 1.70 | 0.1582 | 50 | 2.377 | 35.765 | 0.00 | 0 | | 0.72 | | 0.83 |

TABLE 2-continued

Release rates of substrates loaded with transfluthrin.

| ID | Amount (mg/mL) From GC results | Weight of sample (in g) | Sample extracted in acetone (mL) | Measured sample area (inch$^2$) | TF in mg-per inch$^2$ of substrate | Δ (mg/inch$^2$) | Duration (days) | Release rate of Transflutrhrin μg/inch$^2$hrs | Total amount of TF (g) for 5 × 4 inch$^2$ substrate | Release of TF mg/hrs from 5 × 4 inch$^2$ substrate | Total amount of TF in grams for 5 × 4 inch$^2$ |
|---|---|---|---|---|---|---|---|---|---|---|---|
| D | 0.92 | 0.0690 | 50 | 0.707 | 65.081 | 0.00 | 0 | | 1.30 | | 1.68 |
| E | 4.12 | 0.3867 | 50 | 2.994 | 68.798 | 0.00 | 0 | | 1.38 | | 1.56 |
| F | 5.56 | 0.4650 | 50 | 2.599 | 106.977 | 0.00 | 0 | | 2.14 | | 2.6 |
| | | | | | | | 7 days | | | | |
| A | 1.47 | 0.1455 | 50 | 1.409 | 52.165 | 0.74 | 7 | 4.40 | 1.04 | 0.09 | |
| B | 2.62 | 0.2356 | 50 | 1.71 | 76.622 | 8.01 | 7 | 47.69 | 1.53 | 0.95 | |
| C | 1.70 | 0.1684 | 50 | 2.53 | 33.596 | 2.17 | 7 | 12.89 | 0.67 | 0.26 | |
| D | 1.85 | 0.172 | 50 | 1.762 | 52.500 | 12.58 | 7 | 74.89 | 1.05 | 1.50 | |
| E | 2.50 | 0.2379 | 50 | 1.842 | 67.858 | 0.94 | 7 | 5.60 | 1.36 | 0.11 | |
| F | 2.89 | 0.2697 | 50 | 1.507 | 95.87 | 11.11 | 7 | 66.11 | 1.92 | 1.32 | |
| | | | | | | | 15 days | | | | |
| A | 1.44 | 0.1441 | 50 | 1.395 | 51.597 | 1.31 | 15 | 3.63 | 1.03 | 0.07 | |
| B | 2.07 | 0.1971 | 50 | 1.43 | 72.362 | 12.27 | 15 | 34.09 | 1.45 | 0.68 | |
| C | 1.38 | 0.1682 | 50 | 2.527 | 27.306 | 8.46 | 15 | 23.50 | 0.55 | 0.47 | |
| D | 1.72 | 0.1481 | 50 | 1.517 | 56.687 | 8.39 | 15 | 23.31 | 1.13 | 0.47 | |
| E | 2.02 | 0.2064 | 50 | 1.596 | 63.197 | 5.60 | 15 | 15.56 | 1.26 | 0.31 | |
| F | 2.68 | 0.2733 | 50 | 1.527 | 87.733 | 19.24 | 15 | 53.45 | 1.75 | 1.07 | |
| | | | | | | | 21 days | | | | |
| A | 1.63 | 0.1689 | 50 | 1.636 | 49.829 | 3.08 | 21 | 6.10 | 1.00 | 0.12 | |
| B | 2.02 | 0.193 | 50 | 1.401 | 72.114 | 12.52 | 21 | 24.84 | 1.44 | 0.50 | |
| C | 1.81 | 0.1796 | 50 | 2.698 | 33.542 | 2.22 | 21 | 4.41 | 0.67 | 0.09 | |
| D | 1.87 | 0.1709 | 50 | 1.751 | 53.409 | 11.67 | 21 | 23.16 | 1.07 | 0.46 | |
| E | 1.99 | 0.2556 | 50 | 1.747 | 56.96 | 11.84 | 21 | 23.49 | 1.14 | 0.47 | |
| F | 3.14 | 0.2936 | 50 | 1.641 | 96.684 | 11.29 | 21 | 22.41 | 1.91 | 0.45 | |

Example 2: Effect of Pyrethroid Particle Size on Release Rate

Figure 4A:
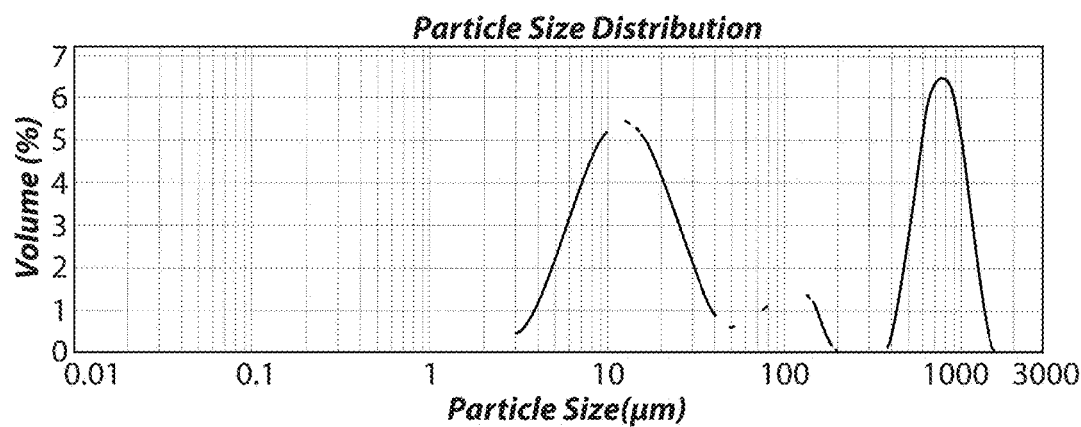
FIGS. 4A-4D show plots of particle size distribution data from the specific embodiment described in Example 2 for pyrethroid particles (4A) dispersed in solution, (4B) in particle form, (4C) after a week of aging, and (4D) when mixed in certain solvents, according to certain embodiments.
Figure 4B:
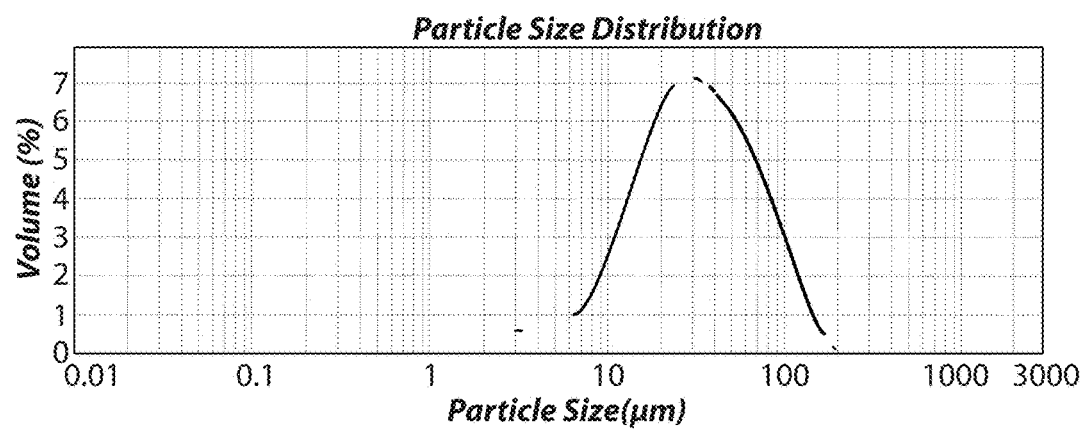
Figure 4C:
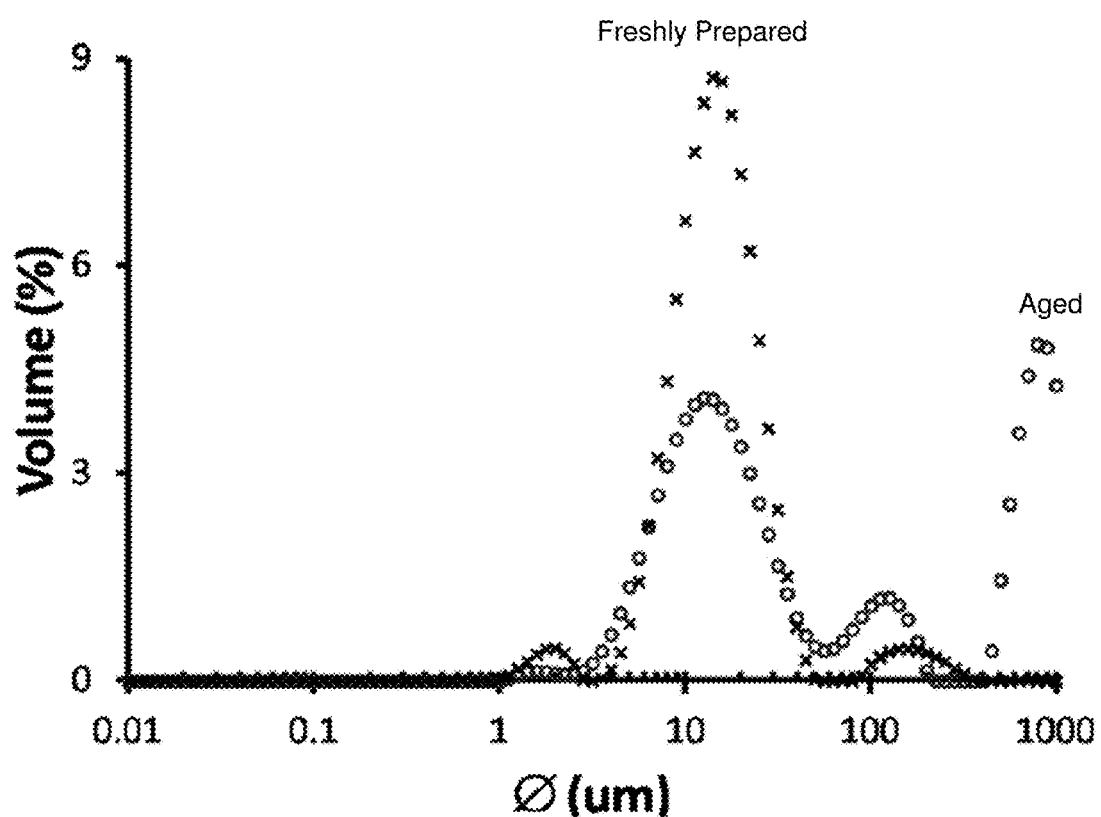

Pyrethroid samples were prepared by (1) suspending evenly dispersing transfluthrin in a solvent (e.g., acetone, hexane), then diluting the solvent with a water and a surfactant to obtain a suspension or (2) suspending and then reconstituting, i.e., by first suspending in acetone, then allowing acetone to evaporate, and then grinding the resulting transfluthrin crystals into a "dust" which is then sifted. Particle size distributions, as measured using Malvern dynamic laser light scattering, for dispersed transfluthrin particles are shown in FIG. 4A. Particle size distributions, as measured using Malvern dynamic laser light scattering, for reconstituted transfluthrin particles are shown in FIG. 4B. Substantially no different in particle size distributions was observed between freshly prepared samples (e.g., samples prepared just before testing) and samples aged for one week (e.g., at 70° F. and 70% relative humidity), as shown in FIG. 4C.

Figure 4D:
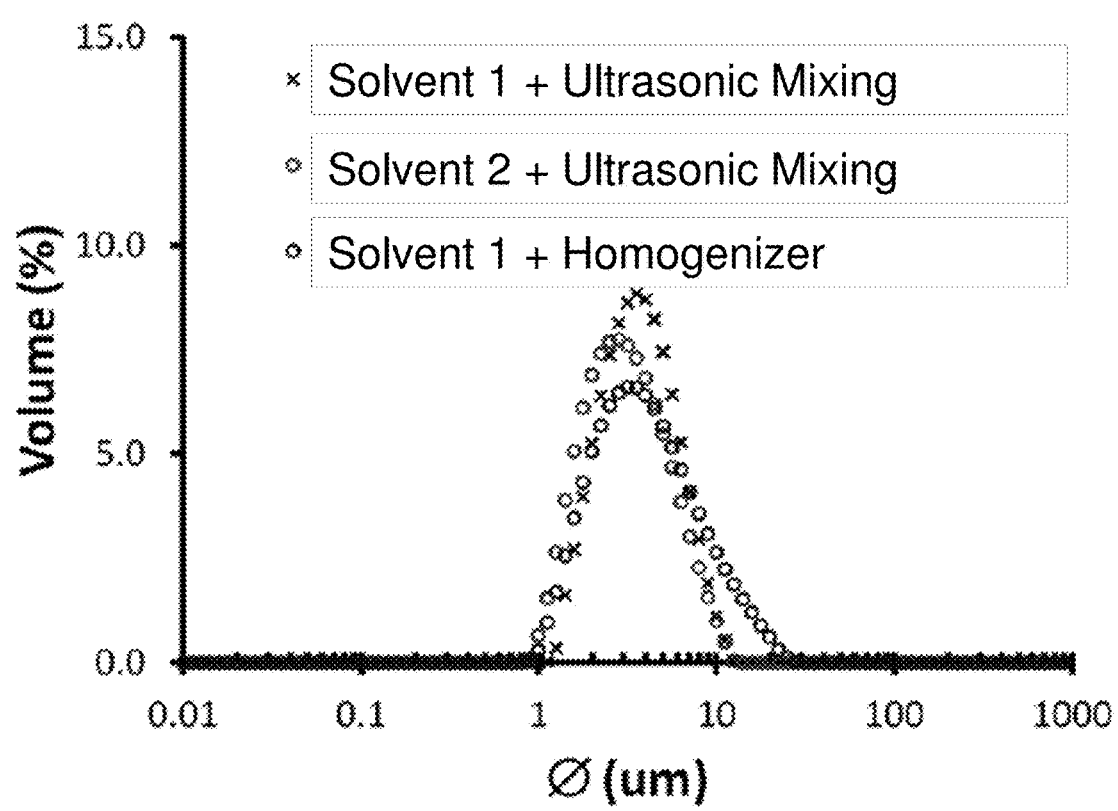

Pyrethroid particles were also prepared by creating a concentrate of 50 wt % transfluthrin and 50 wt % of a solvent (e.g., acetone, hexane). 1 mL of concentrate was then diluted in 100 mL of water and mixed (e.g., using an ultrasonic bath or a homogenizer). Particle size distributions, as measured using Malvern dynamic laser light scattering, for mixed Transfluthrin is shown in FIG. 4D.

Example 3: Mosquito Testing

Samples were prepared containing various Transfluthrin content and a wet dip application, as described herein (as shown in Table 3). Free and Caged mosquitos were exposed to control, 7-day, 14-day, and 21-day aged samples. Mosquito responses (e.g., knock-down, trapped, and killed) are detailed in Table 3.

TABLE 3

Results of mosquito testing.
Summary test results, all mosquito types, days 1, Percent of totals, free-flying, Free-flying Abbott's adjusted

| | Test day | TF content (grams) | Inches Sq (substrate) | Free-flying/ Caged | Average temp/ Humid. | Free-flying | | | Trapped - After 2 hrs Knocked Down | Trapped - After 24 hrs | | |
|---|---|---|---|---|---|---|---|---|---|---|---|---|
| | | | | | | KD* | Trapped | Dead | | Alive | Moribund | Dead |
| Control | 1 | 0.00 | 320 | Free | 86/90 | 0% | 27% | 0% | 49% | 40% | 0% | 60% |
| Room 2 | 1 | 4.02 | 320 | Free | 83/97 | 81% | 5% | 81% | 100% | 0% | 0% | 100% |
| Room 3 | 1 | 4.02 | 320 | Free | 83/97 | 72% | 8% | 72% | 100% | 0% | 0% | 100% |
| Room 4 | 1 | 3.05 | 280 | Free | 85/92 | 68% | 9% | 68% | 100% | 0% | 0% | 100% |

Example 4: Device Preparation

The following example describes fabrication of an exemplary device. An active control device was prepared by cutting 2 in×10 in strips of substrate (e.g., comprising a hydrophilic material and a hydrophobic material). The cut strips were wet-dipped (e.g., in a bath) into a mixture (e.g., comprising a solvent and an aqueous phase), as described herein. The strips were dried at 70° F. and 70% relative humidity in a heat and humidity controlled chamber. The strips were then treated with an acrylate adhesive. Reconstituted, dry pyrethroid was ground through a sieve (e.g., a screen device) and scatted coated on top of the dried strips. Additional adhesive was misted on top of the strips and dried at 80° F. and 70% relative humidity in a heat and humidity controlled chamber. The strips were then rolled and attached to the top of a device (for example, as illustrated in FIG. 2A) using an adhesive. The device was closed and self-adhesive tape is placed on top of the closed device before shrink-wrapping.

Having thus described several aspects of some embodiments of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An insect control device, comprising
   a porous, hydrophobic non-woven material comprising glass fibers; and
   a dry solid insect control composition comprising a pyrethroid;
   wherein the insect control composition is contained within a plurality of pores of the hydrophobic material, such that the hydrophobic material is configured to passively release the pyrethroid for at least 21 days into a surrounding environment, and wherein
   the device does not comprise, and does not require any external energy source for release of the insect control composition comprising a pyrethroid into the surrounding environment.

2. The insect control device of claim 1, wherein the hydrophobic material comprises a pyrethroid selected from the group consisting of transfluthrin, tefluthrin, metofluthrin, allethrin, fenfluthrin, kadethrin, neopynamins, prallethrin, vapothrin, tefluthrin, esbiothrin, dichlovos (DDVP), and combinations thereof.

3. The insect control device of claim 1, wherein the hydrophobic material comprises a pyrethroid comprises transfluthrin.

4. The insect control device of claim 1, wherein the pyrethroid contained within the plurality of pores of the hydrophobic material is in solid particle form.

5. The insect control device of claim 4, wherein the solid particle form results from application to the hydrophobic material of a fluid carrier containing pyrethroid particles with an average particle size between about 1 micron and about 1000 microns, between about 1 micron and about 900 microns, between about 1 micron and about 800 microns, between about 1 micron and about 700 microns, between about 1 micron and about 600 microns, between about 1 micron and about 500 microns, between about 1 micron and about 400 microns, between about 1 micron and about 300 microns, between about 2.5 microns and about 300 microns, between about 2.5 and about 200 microns, between about 2.5 and about 100 microns, or between about 2.5 and about 30 microns, followed by drying.

6. The insect control device of claim 1, wherein the hydrophobic material has a thickness ranging between about 1 micron and about 1000 microns.

7. The insect control device as claim 1, wherein the device further comprises an adhesive material.

8. The insect control device of claim 7, wherein the adhesive material is arranged in physical contact with or adjacent to the hydrophobic material.

9. The insect control device of claim 1, wherein the hydrophobic material is arranged within a sealed container prior to use.

10. The insect control device of claim 1, wherein the insect control device is folded.

11. The insect control device of claim 1, wherein the hydrophobic material has a basis weight of between about 0.5 lbs/100 ft$^2$ and about 4 lbs/100 ft$^2$.

12. The insect control device of claim 1, wherein the release of the pyrethroid as determined by solvent extraction of the pyrethroid from the hydrophobic material followed by measurement of an amount of the pyrethroid extracted, is greater than or equal to 4.41 micrograms per hour per inch$^2$ of the hydrophobic material, and less than or equal to 23.16 micrograms per hour per inch$^2$ of the hydrophobic material after 21 days of release.

13. The insect control device of claim 1, wherein the hydrophobic material initially contains the pyrethroid in an amount of greater than or equal to 41.5 mg per inch$^2$ of the hydrophobic material and less than or equal to 84 mg per inch$^2$ of the hydrophobic material.

14. The insect control device of claim 1, wherein the insect control device provides at least 68% knock down of mosquitos.

15. The insect control device of claim 1, wherein the insect control device provides 100% mortality of trapped mosquitoes within 24 hours of trapping.

16. An insect control device, comprising:
    a non-woven glass fiber substrate and an insect control composition in dry, solid form and comprising a pyrethroid disposed therein,
    wherein the non-woven glass fiber substrate comprises fiberglass staple fibers and a urea-formaldehyde resin binder, and has a basis weight of between about 0.5 lbs/100 ft$^2$ and about 4 lbs/100 ft$^2$; and
    wherein the insect control device is configured to passively release the pyrethroid into a surrounding environment without use of any source of external energy.

17. The insect control device of claim 1, wherein the hydrophobic material is a sheet.

18. The insect control device of claim 1, wherein the hydrophobic material is present within a sealed container.

19. The insect control device of claim 18, wherein the insect control device is configured to release the insect control composition to the surrounding environment upon unsealing of the container.

20. The insect control device of claim 1, wherein the insect control device is configured to repel free-flying insects over a particular area of the surrounding environment.

21. The insect control device of claim 17, wherein the hydrophobic material has a basis weight of between about 0.5 lbs/100 ft$^2$ and about 4 lbs/100 ft$^2$.

22. The insect control device of claim 1, wherein the non-woven material comprising glass fibers comprises fiberglass staple fibers and a urea-formaldehyde resin binder.

23. The insect control device of claim 16, wherein the insect control device is configured to release the pyrethroid for at least 21 days into a surrounding environment.

\* \* \* \* \*